(12) United States Patent
Miyazaki

(10) Patent No.: US 9,572,925 B2
(45) Date of Patent: Feb. 21, 2017

(54) LIQUID TRANSPORTING APPARATUS AND LIQUID TRANSPORTING METHOD

(71) Applicant: SEIKO EPSON CORPORATION, Tokyo (JP)

(72) Inventor: Hajime Miyazaki, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 95 days.

(21) Appl. No.: 14/202,965

(22) Filed: Mar. 10, 2014

(65) Prior Publication Data
US 2014/0261705 A1 Sep. 18, 2014

(30) Foreign Application Priority Data
Mar. 14, 2013 (JP) ................................. 2013-051378

(51) Int. Cl.
| | | |
|---|---|---|
| *A61M 5/14* | (2006.01) | |
| *A61M 5/142* | (2006.01) | |
| *F16K 31/02* | (2006.01) | |
| *A61M 5/168* | (2006.01) | |

(52) U.S. Cl.
CPC ..... *A61M 5/14248* (2013.01); *A61M 5/16804* (2013.01); *A61M 5/16831* (2013.01); *A61M 5/16877* (2013.01); *F16K 31/02* (2013.01); *A61M 2205/3569* (2013.01); *A61M 2205/502* (2013.01); *Y10T 137/0318* (2015.04); *Y10T 137/85978* (2015.04)

(58) Field of Classification Search
CPC ............... F16K 31/02; A61M 5/14248; A61M 5/16877; A61M 5/16804; A61M 2205/502

USPC ..................................................... 251/129.04
See application file for complete search history.

(56) References Cited

U.S. PATENT DOCUMENTS

| | | | | |
|---|---|---|---|---|
| 3,598,288 | A * | 8/1971 | Posgate ........................ | 222/644 |
| 4,210,138 | A * | 7/1980 | Jess et al. ..................... | 604/67 |
| 5,239,319 | A * | 8/1993 | Miyazaki et al. ............ | 340/679 |
| 7,137,964 | B2 | 11/2006 | Flaherty | |
| 7,766,026 | B2 * | 8/2010 | Boey ............................... | 137/1 |
| 7,819,643 | B2 * | 10/2010 | Miyazaki et al. ......... | 417/477.3 |
| 8,303,275 | B2 * | 11/2012 | Miyazaki et al. ......... | 417/477.1 |
| 8,491,283 | B2 * | 7/2013 | Miyazaki et al. ............ | 417/474 |
| 8,491,284 | B2 * | 7/2013 | Miyazaki et al. ............ | 417/474 |
| 8,491,286 | B2 * | 7/2013 | Miyazaki et al. ......... | 417/477.2 |
| 8,926,297 | B2 * | 1/2015 | Miyazaki et al. ............ | 417/474 |
| 9,220,837 | B2 * | 12/2015 | Pesach .............. | A61M 5/14244 |
| 2007/0154336 | A1 * | 7/2007 | Miyazaki et al. ............ | 417/474 |
| 2008/0138218 | A1 * | 6/2008 | Miyazaki et al. ......... | 417/410.3 |
| 2009/0060755 | A1 * | 3/2009 | Miyazaki ...................... | 417/212 |
| 2010/0063438 | A1 * | 3/2010 | Bengtsson ........ | A61M 5/14248 604/66 |
| 2010/0074781 | A1 * | 3/2010 | Miyazaki et al. ............ | 417/474 |

(Continued)

FOREIGN PATENT DOCUMENTS

| | | |
|---|---|---|
| JP | A-2006-511263 | 4/2006 |
| JP | 2007-525241 A | 9/2007 |

(Continued)

*Primary Examiner* — Matthew W Jellett
(74) *Attorney, Agent, or Firm* — Oliff PLC

(57) ABSTRACT

A liquid transporting apparatus includes a driving section that transports a the liquid; a control section that controls the driving section, based on a control pattern; and an operation section that is operated to change the control pattern for controlling the driving section.

20 Claims, 16 Drawing Sheets

(56) References Cited

U.S. PATENT DOCUMENTS

| | | | |
|---|---|---|---|
| 2011/0305588 A1* | 12/2011 | Miyazaki et al. | 417/474 |
| 2013/0274576 A1* | 10/2013 | Amirouche | A61M 5/1408 600/365 |
| 2014/0213975 A1* | 7/2014 | Clemente | A61M 5/158 604/151 |

FOREIGN PATENT DOCUMENTS

| | | |
|---|---|---|
| JP | A-2010-534085 | 11/2010 |
| WO | WO 2004/056412 A2 | 7/2004 |
| WO | 2004/093648 A2 | 11/2004 |
| WO | WO 2009/013736 A1 | 1/2009 |

* cited by examiner

LIQUID TRANSPORTING APPARATUS AND LIQUID TRANSPORTING METHOD

BACKGROUND

1. Technical Field

The present invention relates to a liquid transporting apparatus and a liquid transporting method.

2. Related Art

There is a liquid transporting apparatus capable of continuously transporting a liquid. As a practical example of the liquid transporting apparatus, an insulin injecting apparatus is known which is used when a liquid medicine such as insulin is continuously and subcutaneously injected inside a body. When the insulin is subcutaneously injected by using such a liquid transporting apparatus, it is necessary to control an injection amount of the insulin. For example, a liquid transporting apparatus is disclosed in JP-A-2006-511263, which is capable of controlling a transporting the proper amount of the liquid to regularly inject the insulin at a constant flow (basal) and to increase the injection amount (bolus) after the patient takes a meal or the like, based on operation commands which are programmed in advance.

Control of the injection amount of the insulin is usually performed by changing a program regarding the operation commands. However, since a body of the liquid transporting apparatus is required to be small, it is difficult to provide an operation section or a display section for changing the program in the body of the apparatus. Therefore, the change in the program is often done using an external controller or the like which is separate from the body of the liquid transporting apparatus. However, when adjustment of the injection amount of the insulin is necessary suddenly in somewhere or the like for a user of the liquid transporting apparatus, it is difficult to easily adjust the injection amount (the transporting amount) of the insulin in the liquid transporting apparatus by a single unit, if the user does not carry the external controller at hand.

SUMMARY

An advantage of some aspects of the invention is to provide a small liquid transporting apparatus capable of easily adjusting a transporting amount by a single unit.

A liquid transporting apparatus according to an aspect of the invention includes: a driving section that transports a liquid by squeezing a transporting tube for transporting the liquid; a control, section that controls an operation of the driving section, based on one of a plurality of control patterns which are set in advance; and a body section that holds the driving section and the control section, and has a button for changing the control patterns for controlling the operation of the driving section, and does not have a unit displaying information regarding the transportation of the liquid.

Other features of the invention will be apparent from the following description and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
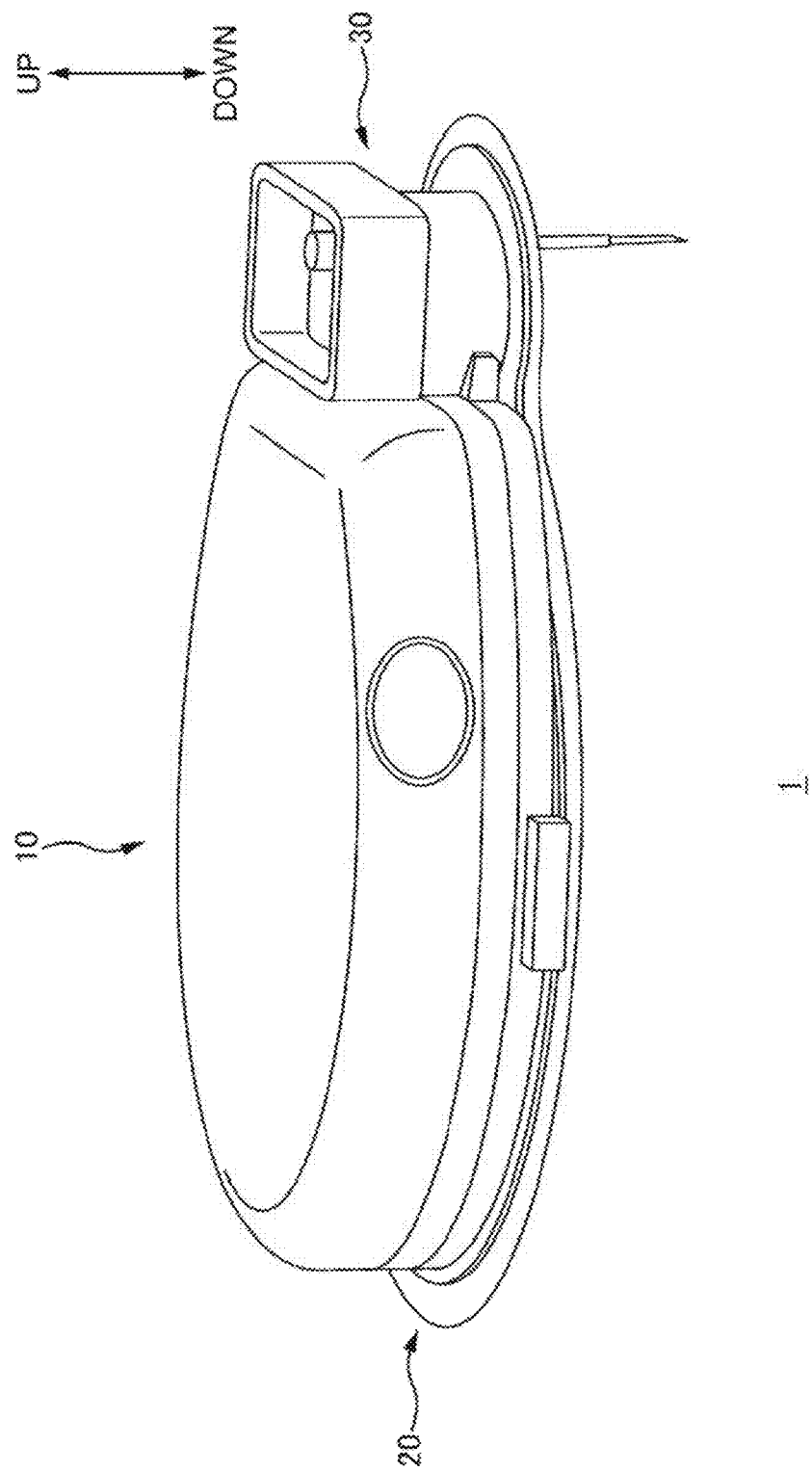
FIG. 1 is an overall perspective view of a liquid transporting apparatus.

The matters will become clear by the following description of the specification and the accompanying drawings.

An embodiment of the invention is directed to a liquid transporting apparatus including: a driving section that transports a liquid by squeezing a transporting tube for transporting the liquid; a control section that controls an operation of the driving section, based on one of a plurality of control patterns which are set in advance; and a body section that holds the driving section and the control section, and has a button for changing the control patterns for controlling the operation of the driving section, and does not have a unit for displaying information regarding the transportation of the liquid.

In this case, it is possible to easily adjust the transporting amount (for example, the injection amount of the insulin) of the liquid by the apparatus of a single unit.

Further, in the liquid transporting apparatus, it is preferable that the button be capable of setting a plurality of functions and a predetermined function of a plurality of functions which are set in the button be realized when the button is pressed.

In this case, even if the user does not carry the external control device (the controller), it is possible to realize various types of functions by the liquid transporting apparatus of the single unit.

Further, in the liquid transporting apparatus, it is preferable that the control section can realize a predetermined function of the plurality of functions which are set in the button depending on a length of a time the function button is pressed.

In this case, occurrence of malfunction due to erroneous operation by the user is easily suppressed.

Further, in the liquid transporting apparatus, it is preferable that the function of the button be set by using the external control device that remotely controls the liquid transporting apparatus from outside.

In this case, even if the liquid transporting apparatus does not include the display section such as the display, it is possible to accurately perform the setting of the function. Further, various types of functions including the setting of the control pattern are easily set.

Further, in the liquid transporting apparatus, it is preferable that the function for adjusting the liquid transport amount or the function for stopping quickly the transporting operation of the liquid be set by changing the control pattern.

In this case, it is easy to change the liquid transport amount at the time of patient taking a meal or the like with respect to the liquid transport amount based on a usual control pattern, or to stop quickly the transporting operation amount of the liquid. That is, even if the user does not carry the controller, it is possible to easily adjust the transporting amount of the liquid (for example, the injection amount of the insulin) by the liquid transporting apparatus of the single unit.

Further, another embodiment of the invention is directed to a liquid transporting method including: transporting a liquid by squeezing a transporting tube for transporting the liquid; controlling an operation which squeezes the transporting tube, based on one of a plurality of control patterns which are set in advance; and changing the control pattern for controlling the operation which squeezes the transporting tube when the button is pressed included in the body section that does not have a unit for displaying information regarding the transportation of the liquid.

First Embodiment

Basic Configuration of Liquid Transporting Apparatus

Figure 2:
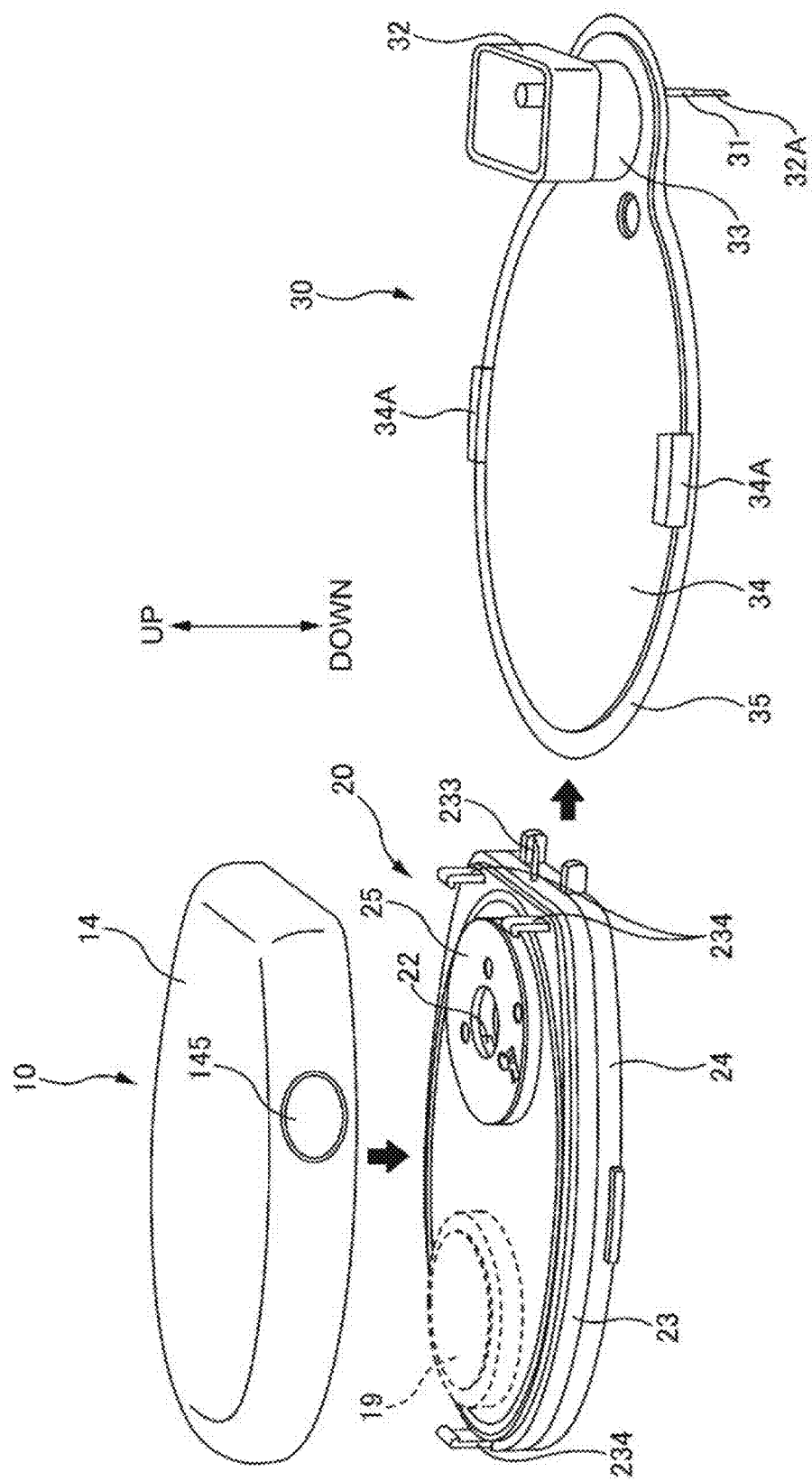
FIG. 2 is an exploded view of the liquid transporting apparatus.

FIG. 1 is an overall perspective view of a liquid transporting apparatus 1. FIG. 2 is an exploded view of the liquid transporting apparatus 1. As illustrated in the views, description is given in which a side (a side of a living body) where the liquid transporting apparatus 1 is adhered is referred to as "down" and the side opposite the living body is referred to as "up."

The liquid transporting apparatus 1 is an apparatus for transporting a liquid. The liquid transporting apparatus 1 includes a body 10, a cartridge 20 and an injection set 30. Further, a controller 50 (see FIG. 11) for remotely controlling the liquid transporting apparatus 1 from outside is included.

As illustrated in FIG. 2, the body 10, the cartridge 20 and the injection set 30 can be separated from each other, but as illustrated in FIG. 1, they are integrally assembled when being used. The liquid transporting apparatus 1 is appropriately used to periodically inject insulin stored in the cartridge 20 by adhering the injection set 30 to the living body. If the liquid (for example, the insulin) stored in the cartridge 20 runs out, the cartridge 20 is replaced. Further, the injection set 30 is generally replaced once in every three day. Meanwhile, the body 10 may be continuously used.

Figure 3:
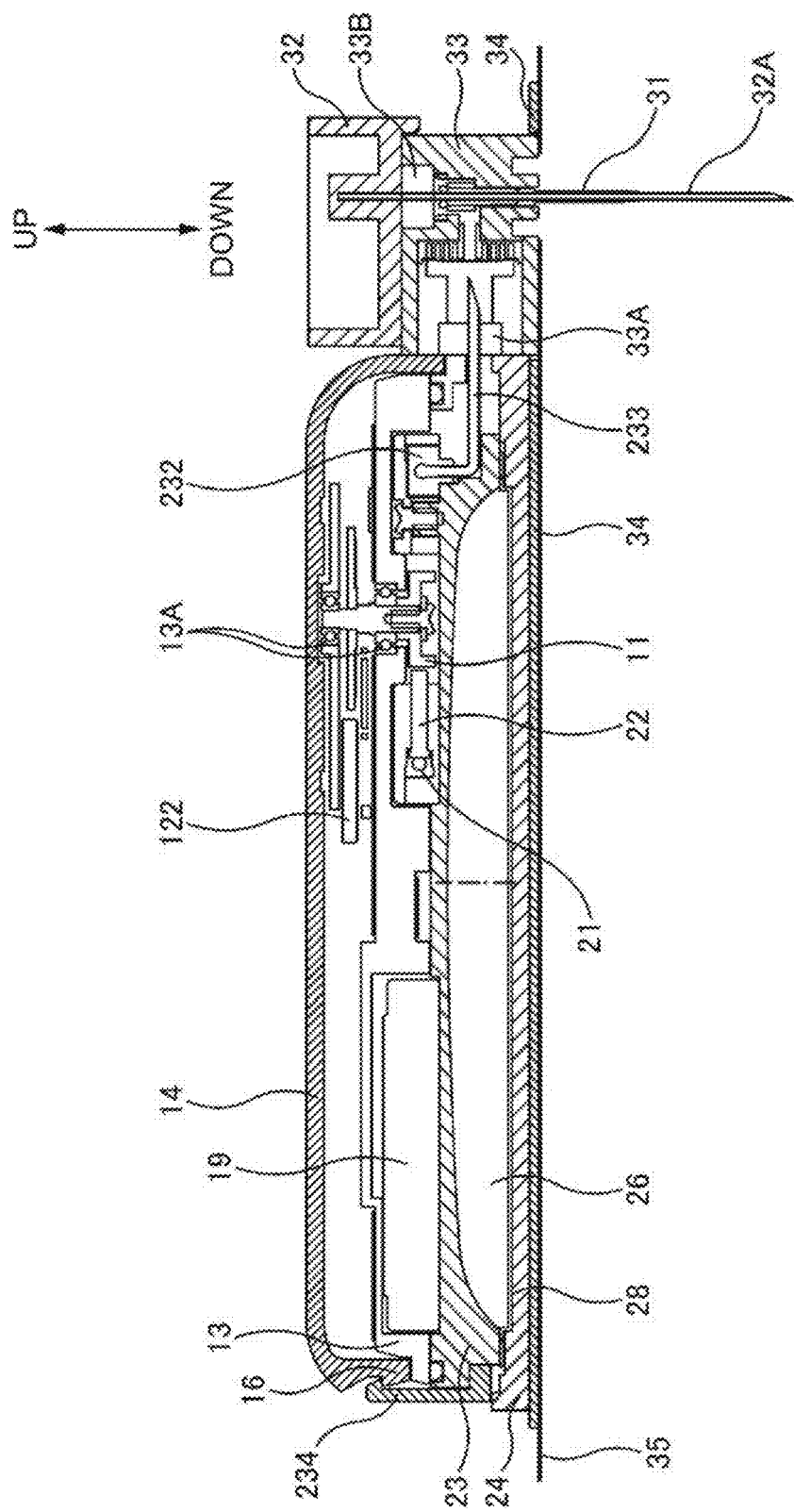
FIG. 3 is a cross-sectional view of the liquid transporting apparatus.
Figure 4:
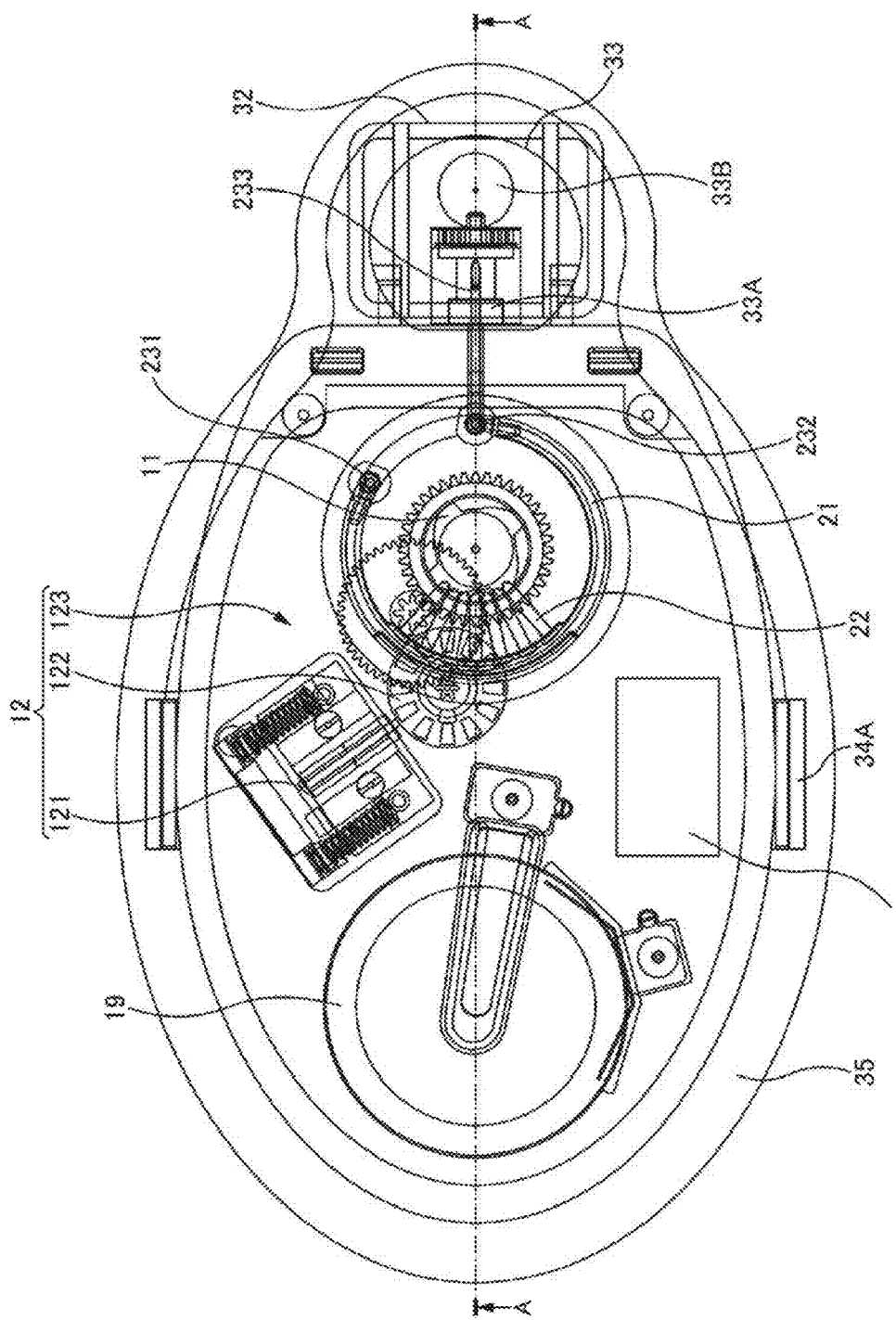
FIG. 4 is a transparent top view of an inside of the liquid transporting apparatus.
Figure 5:
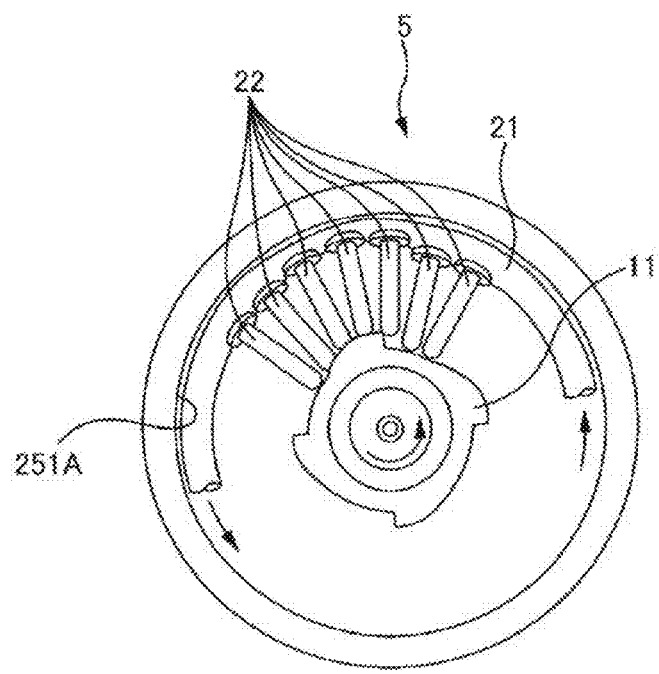
FIG. 5 is a schematic explanatory view of a driving section.

FIG. 3 is a cross-sectional view of the liquid transporting apparatus 1. FIG. 4 is a transparent top view of an inside of the liquid transporting apparatus 1. In FIG. 4, a configuration of a driving section 5 (described below in detail) is illustrated. FIG. 5 is a schematic explanatory view of the driving section 5.

The driving section 5 has a function as a pump for transporting the liquid stored in the cartridge 20. The driving section 5 of the embodiment includes a cam 11 and a driving mechanism 12, and transports the liquid by squeezing a tube 21 by driving a plurality of fingers 22.

The tube 21 is a transporting tube for transporting the liquid. An upstream side (an upstream side when being based on a transportation direction of the liquid) of the tube 21 communicates with a storage section 26 of the liquid of the cartridge 20. The tube 21 has elasticity enough to be closed when being pressed by the finger 22 and to be returned to an original position when releasing a force from the finger 22. The tube 21 is partially disposed in a circular arc shape along an inner surface of a tube guide wall 251A of the cartridge 20. The portion of the circular arc shape of the tube 21 is disposed between the inner surface of the tube guide wall 251A and the plurality of fingers 22. A center of a circle of the tube 21 is coincident with a rotation center of the cam 11.

The finger 22 is a member for closing the tube 21. The finger 22 is operated in a driven basis by receiving a force from the cam 11. The finger 22 has a rod-shaped shaft section and a collar-shaped pressing section, and is a T-shape. The rod-shaped shaft section comes into contact with the cam 11 and the collar-shaped pressing section comes into contact with the tube 21. The finger 22 is supported so as to be movable along an axial direction. As illustrated in FIG. 5, in the embodiment, the plurality of fingers 22 are radially disposed between the cam 11 and the tube 21 at an equal distance from the rotation center of the cam 11.

The cam 11 has protrusion sections at four positions of an outer periphery thereof. The plurality of fingers 22 are disposed on the outer periphery of the cam 11 and the tube 21 is disposed outside the fingers 22. The tube 21 is closed by pressing the fingers 22 by the protrusion sections of the cam 11. If the finger 22 is disengaged from the protrusion section, the tube 21 returns to the original shape by an elastic force of the tube 21. If the cam 11 rotates, seven fingers 22 are pressed in order from the protrusion section and then the tube 21 closes from the upstream side in order in the transportation direction. Therefore, the tube 21 performs writhing and the liquid is squeezed and transported by the tube 21. In order to prevent backflow of the liquid, the protrusion sections of the cam 11 are formed so that at least one and preferably two fingers 22 close the tube 21.

The driving mechanism 12 is a mechanism for driving the rotation of the cam 11. The driving mechanism 12 has a piezoelectric motor 121, a rotor 122 and a reduction transmission device 123 (see FIG. 4).

The piezoelectric motor 121 is a motor for rotating the rotor 122 by using vibration of a piezoelectric element. The piezoelectric motor 121 vibrates a vibration body by applying a drive signal to the piezoelectric element that is adhered to both surfaces of a rectangular vibration body. An end section of the vibration body comes into contact with the rotor 122 and the end section vibrates while drawing a predetermined orbit such as an elliptic orbit or an S-shaped orbit, if the vibration body vibrates. The end section of the vibration body comes into contact with the rotor 122 in a part of the vibration orbit and then the rotor 122 is driven to rotate. The piezoelectric motor 121 is biased toward the rotor 122 by a pair of springs so that the end section of the vibration body comes into contact with the rotor 122.

The rotor 122 is a driven body that is rotated by the piezoelectric motor 121. A rotor pinion that configures a part of the reduction transmission device 123 is formed in the rotor 122.

The reduction transmission device 123 is a device that transmits the rotation of the rotor 122 to the cam 11 with a predetermined reduction ratio. The reduction transmission device 123 is configured of a rotor pinion, a transmission wheel and a cam gear. The rotor pinion is a small gear which is integrally attached to the rotor 122. The transmission wheel has a large gear that meshes with the rotor pinion and a pinion that meshes with the cam gear, and has a function for transmitting a rotational force of the rotor 122 to the cam 11. The cam gear is integrally attached to the cam 11 and is rotatably supported with the cam 11.

Hereinafter, configurations of the body 10, the cartridge 20, the injection set 30 and the controller 50 are described.

Body 10

Figure 6:
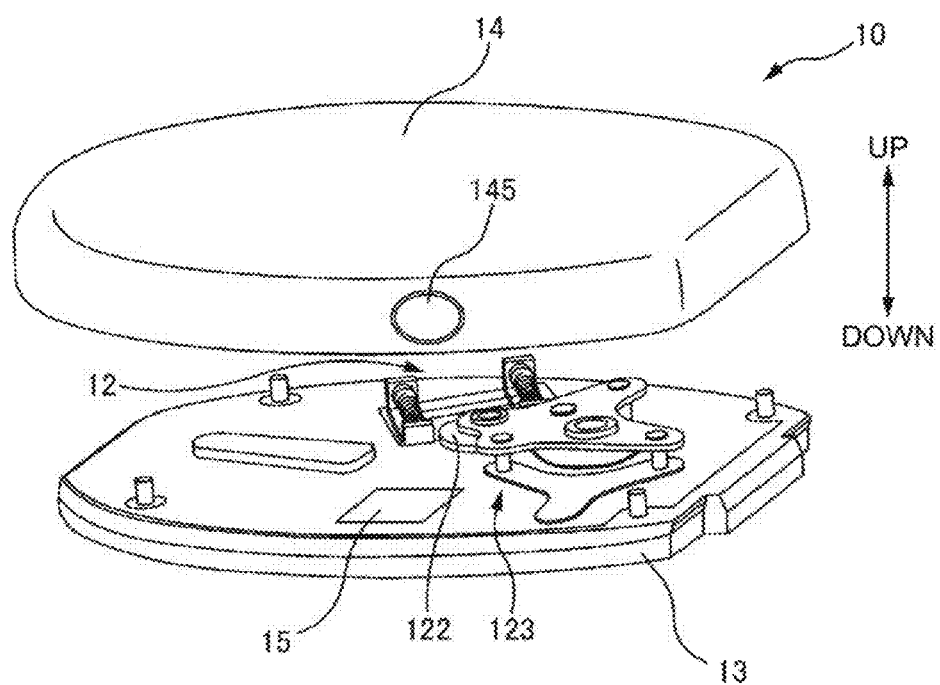
FIG. 6 is an exploded perspective view illustrating an internal structure of a body.
Figure 7:
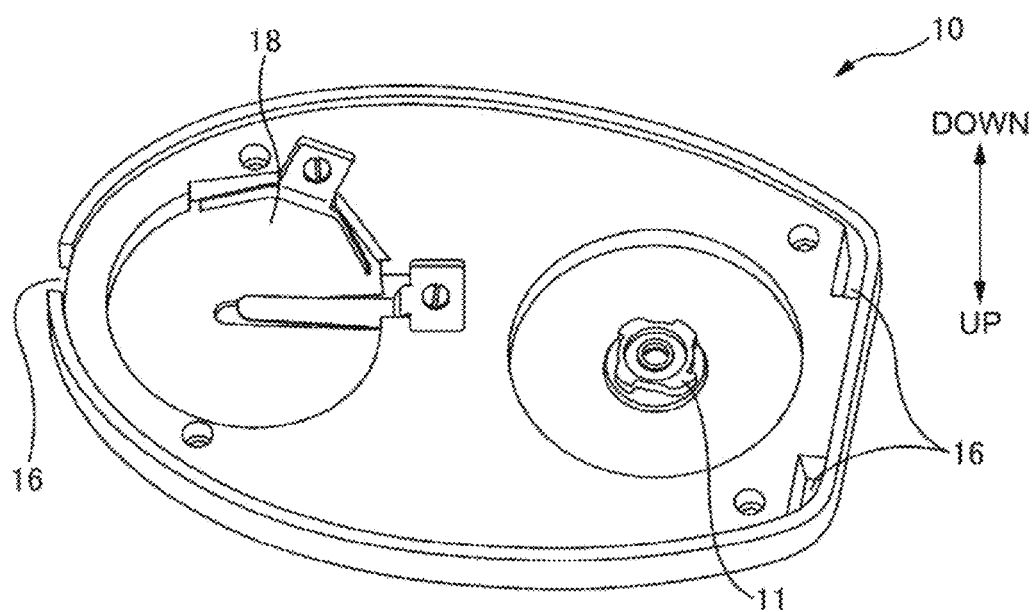
FIG. 7 is a perspective view of a back surface of the body.

FIG. 6 is an exploded perspective view illustrating a configuration of an inside of the body 10. FIG. 7 is a perspective view of a back surface of the body 10. Hereinafter, the configuration of the body 10 is described with reference to FIGS. 1 to 4 and those drawings.

The body 10 has a body base 13 and a body case 14. Then, the driving mechanism 12 described above and a control substrate 15 described below are maintained on the body base 13. Further, a bearing 13A is provided in the body base 13. A rotation shaft of the cam 11 passes through the body base 13 and the bearing 13A rotatably supports the rotation shaft of the cam 11 with respect to the body base 13. The cam 11 is integrally formed with the cam gear configuring the reduction transmission device 123 and the cam gear is disposed inside the body 10 by being covered by the body case 14, and the cam 11 is exposed from the body 10. If the body 10 and the cartridge 20 are combined together, the cam 11 which is exposed from the body 10 meshes with the end section of the finger 22 of the cartridge 20.

The body case 14 is a member configuring an exterior of the liquid transporting apparatus 1. The driving mechanism 12 (the piezoelectric motor 121, the rotor 122 and the reduction transmission device 123) or the control substrate 15 provided in the body base 13 is covered and protected by the body case 14.

In the embodiment, a function button 145 is provided in the body case 14. The function button 145 is a button which can set a plurality of functions and can realize any function which is set when the button is pressed. The function button 145 of the embodiment has functions which perform switching of a plurality of control patterns which are set in the control substrate 15 and the detailed description thereof is given below. Moreover, setting of the functions of the function button 145 is done using the controller 50.

Further, as illustrated in FIG. 6, the function button 145 is preferably provided in the side section of the body case 14. In the embodiment, since the function button 145 is conceivable to be operated (pressed) in a state where the body 10 is mounted on the living body, if the function button 145 is provided in an upper section of the body case 14 or the like, a positional relationship in which a pressing direction (downward direction in FIG. 6) of the button faces the living body is given. That is, since the button is pressed against the skin in a pressing direction, a load is likely applied to the living body. Meanwhile, as illustrated in FIG. 6, if the function button 145 is provided in the side section of the body case 14, since the button is pressed so as to pinch both sides of the body case 14 when a user presses the button, the load is unlikely applied to the living body.

Further, in the embodiment, a display such as a liquid crystal display is not provided in the body case 14. That is, the body 10 does not have a unit (a display section) for displaying information regarding the transportation of the liquid. If the liquid transporting apparatus 1 is used as an insulin injecting apparatus, since it is often used being mounted on the body (the living body) of the user, the body of the apparatus are required to be in small size and in light weight. In the embodiment, since the display section is not provided in the body 10, it is possible to configure the liquid transporting apparatus 1 in the small size and the light-weight.

The control substrate 15 is a control section that controls an operation of the driving section 5. A storage section (a memory) capable of storing a plurality of control patterns (control programs) for controlling the piezoelectric motor 121 described above or the like is provided in the control substrate 15. Then, the cam 11 is driven, based on one of the plurality of control patterns stored in the storage section, and writhing of the tube 21 is controlled by the finger 22. The user can change a liquid transport amount by selecting arbitrary control pattern which is set in advance and detailed description thereof is given below. That is, an injection amount (injection unit) of the insulin can be adjusted. Moreover, the control patterns are set by using the controller 50 described below.

A hook hanger 16 is provided in the body 10. A fixed hook 234 of the cartridge 20 is caught on the hook hanger 16 and the body 10 is fixed to the cartridge 20. Further, the body 10 has a battery storage section 18. A battery 19 stored in the battery storage section 18 is a power source of the liquid transporting apparatus 1.

Further, a receiving section (not illustrated) for receiving a signal or a radio wave that is transmitted from the controller 50 described below is provided in the body 10.

Cartridge 20

Figure 8:
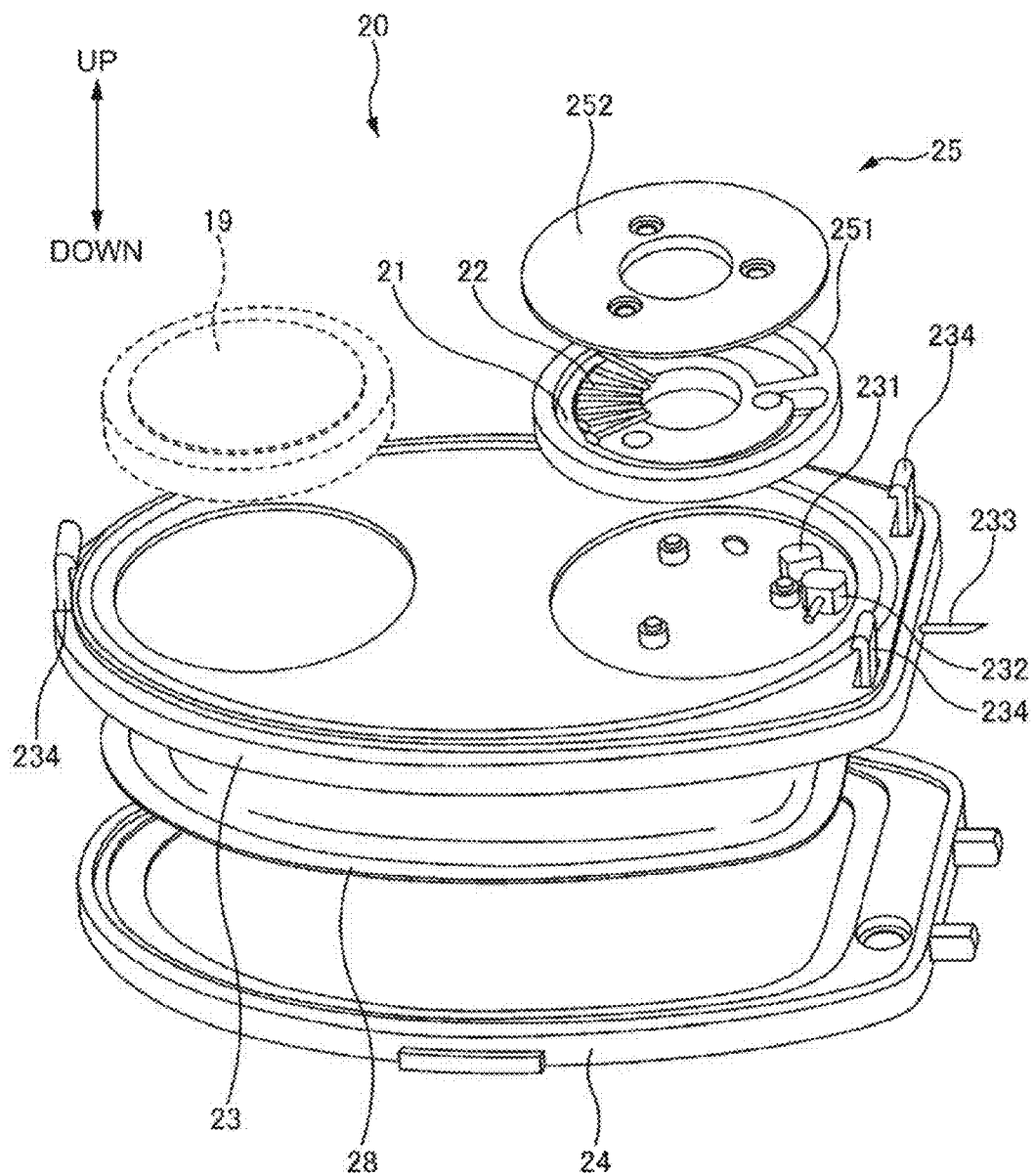
FIG. 8 is an exploded perspective view illustrating an internal structure of a cartridge.
Figure 9:
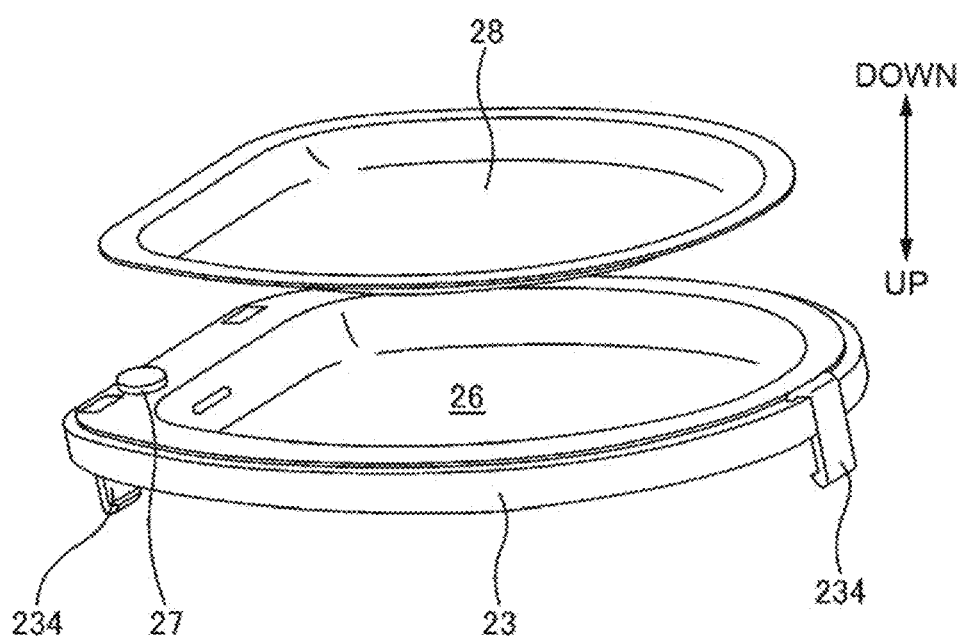
FIG. 9 is an exploded perspective view of a back surface of a base of the cartridge.

FIG. 8 is an exploded perspective view illustrating a configuration of an inside of the cartridge 20. FIG. 9 is an exploded perspective view of a back surface of the cartridge 20. Hereinafter, a configuration of the cartridge 20 is described with reference to FIGS. 1 to 5 and those drawings.

The cartridge 20 has a cartridge base 23 and a base receiver 24.

A tube unit 25 is provided on an upper side of the cartridge base 23. The tube unit 25 has the tube 21 and the plurality of fingers 22 which are described above, a unit base 251 and a unit cover 252. The tube guide wall 251A is formed in the unit base 251 and the tube 21 is disposed inside the unit base 251 in a circular arc shape. Further, the unit base 251 movably supports the fingers 22 in the axial direction. The tube 21 and the fingers 22 inside the unit base 251 are covered by the unit cover 252.

The tube unit 25 is a planar cylindrical shape and the cam 11 exposed from the body 10 is inserted into a cavity of a center of the tube unit 25. Therefore, the cam 11 on the side of the body 10 meshes with the fingers 22 on the side of the cartridge 20.

A supply-side joint 231 and a discharge-side joint 232 are provided in the cartridge base 23. End sections of the tube 21 inside the tube unit 25 are connected to the supply-side joint 231 and the discharge-side joint 232, respectively if the plurality of fingers 22 squeeze the tube 21 in order, the liquid is supplied from the supply-side joint 231 to the tube 21 and the liquid is discharged from the discharge-side joint 232. A connection needle 233 communicates with the discharge-side joint 232 and the liquid discharged from the discharge-side joint 232 is supplied on the side of the injection set 30 through the connection needle 233.

The fixed hook 234 is formed in the cartridge base 23. The fixed hook 234 is caught on the hook hanger 16 of the body 10 and fixes the body 10 to the cartridge 20.

A reservoir film 28 is interposed between the cartridge base 23 and the base receiver 24. Circumference of the reservoir film 28 comes into close contact with a bottom surface of the cartridge base 23. The storage section 26 is formed between the cartridge base 23 and the reservoir film 28, and the liquid (for example, the insulin) is stored in the storage section 26. The storage section 26 communicates with the supply-side joint 231 and the liquid stored in the storage section 26 is supplied to the tube 21 through the supply-side joint 231.

As described above, the storage section 26 is configured on the lower side of the cartridge base 23. Since the tube 21 and the fingers 22 configuring the driving section 5 are disposed on the upper side of the cartridge base 23, the driving section 5 and the storage section 26 are disposed up and down. Therefore, the small size of the liquid transporting apparatus 1 is achieved. Further, the storage section 26 is disposed on the side of the living body from the driving section 5. Therefore, the liquid stored in the storage section 26 is likely to keep a temperature with a temperature of the living body and a difference between the temperature of the liquid and the temperature of the living body is suppressed.

If the liquid stored in the storage section 26 runs out, the cartridge 20 is detached from the liquid transporting apparatus 1 and is replaced with new cartridge 20. However, the liquid can be injected from outside into the storage section 26 through a cartridge septum 27 using an injection needle. Moreover, the cartridge septum 27 is configured of a material (for example, rubber, silicon or the like) that closes a hole if the injection needle is pulled out.

Injection Set 30

Figure 10:
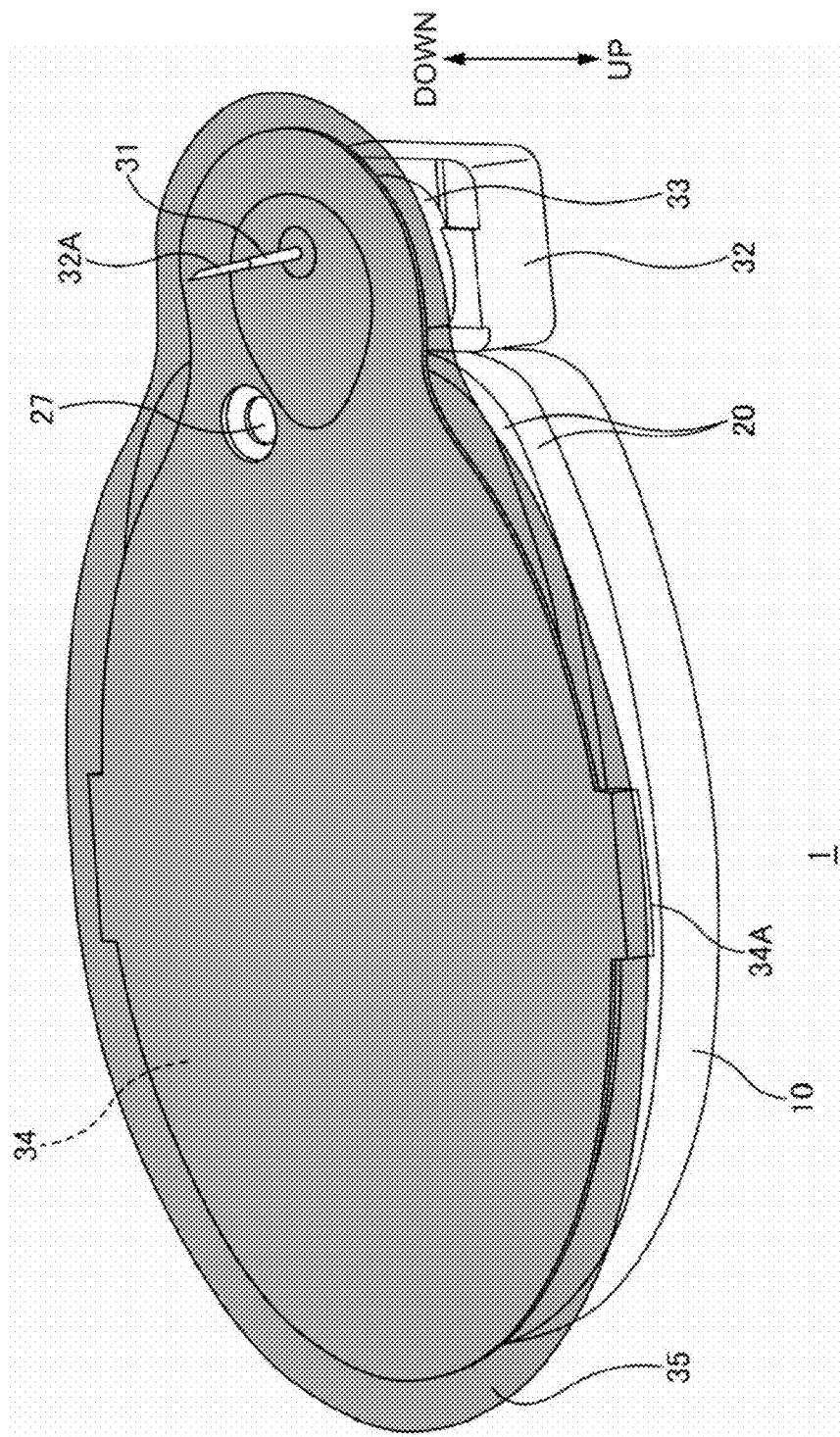
FIG. 10 is a perspective view in which the liquid transporting apparatus is viewed from a side of a bottom surface of an injection set.

FIG. 10 is a perspective view of the liquid transporting apparatus 1 viewed from a side of the bottom surface of the injection set 30. Hereinafter, a configuration of the injection set 30 is described with reference to FIGS. 1 to 5.

The injection set 30 has a soft needle 31, an introduction needle folder 32, a port base 33, an injection set base 34 and an adhesive pad 35.

The soft needle 31 is a tube for injecting the liquid into the living body and has a function of a catheter. For example, the soft needle 31 is configured of a soft material such as fluorine resin. An end of the soft needle 31 is fixed to the port base 33.

The introduction needle folder 32 is a member for maintaining an introduction needle 32A. An end of the introduction needle 32A is fixed to the introduction needle folder 32. The introduction needle 32A is a needle made of a metal for inserting the soft needle 31 which is soft into the living body. The introduction needle 32A is a hollow tubular needle which is long and narrow, and has a transverse hole (not illustrated). If the liquid is supplied from the transverse hole of the introduction needle 32A, the liquid is discharged from a leading end of the introduction needle 32A. Therefore, before the soft needle 31 punctures the living body, priming processing which fills the inside a flow path of the liquid transporting apparatus 1 with the liquid can be performed.

In a state prior to use, the introduction needle folder 32 is attached to the port base 33, the introduction needle 32A is inserted into the soft needle 31 and then a needle tip is exposed from the lower side of the soft needle 31. When the injection set 30 is attached to the living body, after the soft needle 31 and the introduction needle 32A puncture the living body, the introduction needle folder 32 is withdrawn (removed) from the port base 33 for each introduction needle 32A. Since the introduction needle 32A which is hard does not need to be continuously placed in the living body, a load on the living body is small. Moreover, since the soft needle 31 is continuously placed on the living body but the soft needle 31 is soft, the load on the living body is small.

The port base 33 is a member that supplies the liquid supplied from the connection needle 233 of the cartridge 20 to the soft needle 31. The port base 33 has a connection needle septum 33A and an introduction needle septum 33B. The connection needle septum 33A and the introduction needle septum 33B are configured of a material (for example, rubber, silicon or the like) that closes the hole if the needle is pulled out. The connection needle 233 of the cartridge 20 is inserted into the connection needle septum 33A and the liquid is supplied from the side of the cartridge 20 to the side of the injection set 30 through the connection needle 233 over the connection needle septum 33A. Even if the connection needle 233 of the cartridge 20 is pulled out from the injection set 30 to replace the cartridge 20, the hole is closed naturally by the connection needle 233 of the connection needle septum 33A. The introduction needle 32A is inserted into the introduction needle septum 33B and if the introduction needle 32A is pulled out, the hole is closed naturally by the introduction needle 32A of the introduction needle septum 33B. The liquid inside the injection set 30 is prevented from leaking to the outside or a body liquid of the living body is prevented from flowing back to the side of the injection set 30 by the connection needle septum 33A and the introduction needle septum 33B. Moreover, a region (a region except the introduction septum) in which the introduction needle 32A is present inside the port base 33 is a flow path of the liquid after the introduction needle 32A is pulled out.

The injection set base 34 is a planar member fixed to the port base 33. The injection set base 34 has a fixing section 34A for fixing the base receiver 24. The adhesive pad 35 is attached to the bottom surface of the injection set base 34. The adhesive pad 35 is an adhesive pad for adhering the injection set 30 to the living body or the like.

Controller 50

Figure 11:
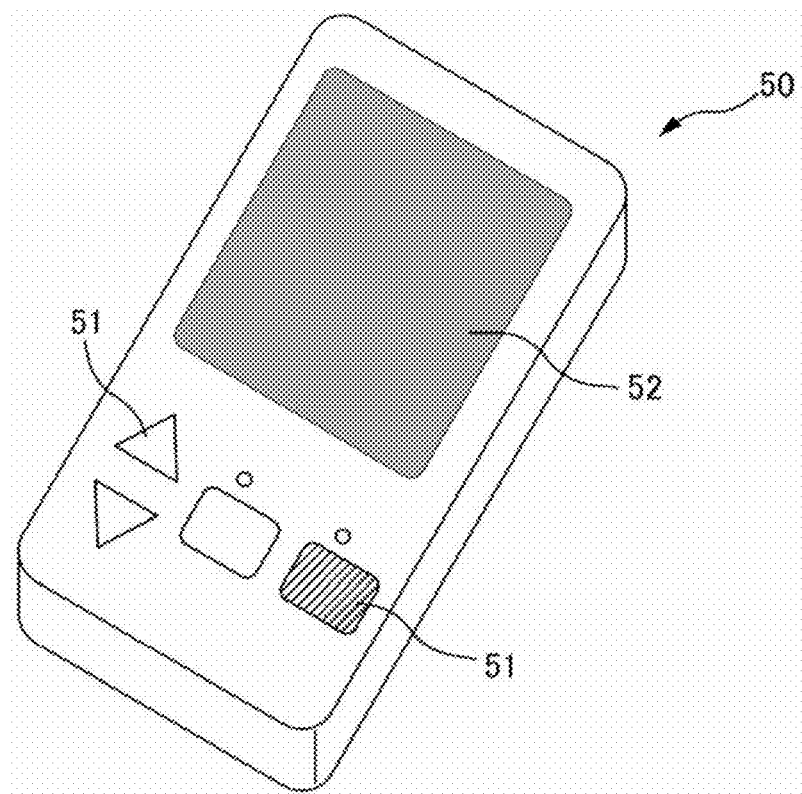
FIG. 11 is a schematic view illustrating an example of a controller.

FIG. 11 is a schematic view illustrating an example of the controller 50. The controller 50 is an external control device that makes the liquid transporting apparatus 1 perform the liquid transportation operation or sets the functions and, for example, is capable of remotely operating the liquid transporting apparatus 1 using wireless communication such as "Bluetooth" (registered trademark) or "ZigBee" (registered trademark), or infrared beams. The controller 50 has operation buttons 51 and a display section 52.

The user can set start/stop of the liquid transportation operation or the control patterns (programs) defining the liquid transport amount per unit time or the like by operating the operation buttons 51. Information (for example, information indicating the transporting amount of the liquid) regarding the liquid transportation operation is displayed on the display section 52 and the user can perform various types of setting while recognizing the information which is displayed. Moreover, in the embodiment, since the display section is not provided on the side of the body 10 of the liquid transporting apparatus 1, the information regarding the liquid transportation operation is basically displayed on the display section 52 of the controller 50. Further, it is possible to display a present time, an alarm concerning the liquid transportation operation or the like on the display section 52.

Using Method of Liquid Transporting Apparatus

Figure 12:
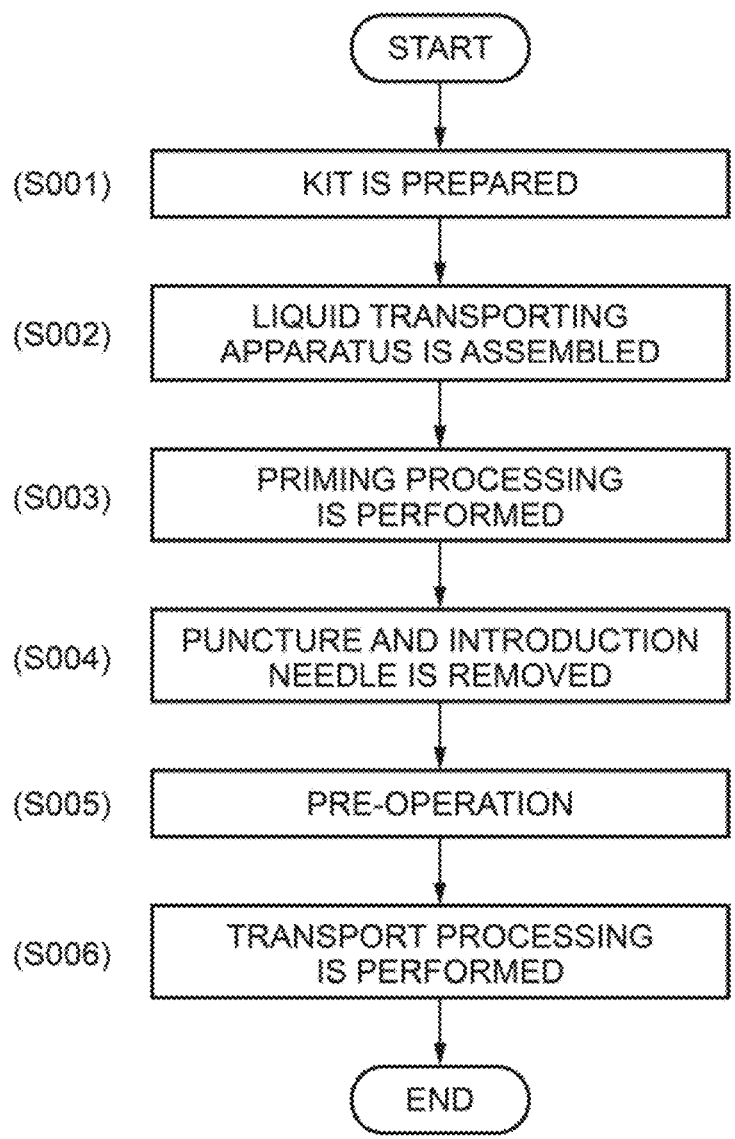
FIG. 12 is a flowchart illustrating a using method of the liquid transporting apparatus.

FIG. 12 is a flowchart illustrating a using method of the liquid transporting apparatus 1.

First, the user prepares a kit of the liquid transporting apparatus 1 (S001). The body 10, the cartridge 20, the injection set 30 or the like for configuring the liquid transporting apparatus 1 is included in the kit. As illustrated in FIG. 2, the user assembles the liquid transporting apparatus 1 by assembling the body 10, the cartridge 20 and the injection set 30 (S002). The user makes the cam 11 on the side of the body 10 mesh with the fingers 22 on the side of the cartridge 20 by assembling the body 10 and the cartridge 20. Further, the user inserts the connection needle 233 of the cartridge 20 into the connection needle septum 33A of the injection set 30 and makes the liquid be capable of supplying from the side of the cartridge 20 to the side of the injection set 30.

Figure 13:
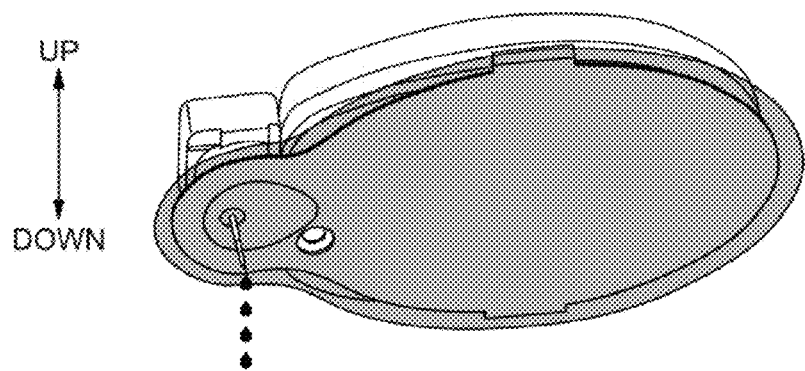
FIG. 13 is an explanatory view of a priming processing.

Next, the user performs the priming processing (S003). FIG. 13 is an explanatory view of the priming processing. The priming processing is a processing that fills the inside the flow path of the liquid transporting apparatus 1 with the liquid by driving the driving section 5 of the liquid transporting apparatus 1. Gas inside the flow path of the liquid transporting apparatus 1 is discharged from the introduction needle 32A by the priming processing. Further, the tube 21 which is vacant by the priming processing is filled with the liquid. The user drives the driving section 5 of the liquid transporting apparatus 1 until the liquid is discharged from the leading end of the introduction needle 32A.

After the priming processing, the user makes the introduction needle 32A and the soft needle 31 puncture perpendicularly the living body, after that, withdraws the introduction needle folder 32 from the port base 33, and removes the introduction needle 32A from the soft needle 31 (S004). Since there is the introduction needle septum 33B, even if the introduction needle 32A is removed, the hole is closed naturally by the introduction needle 32A of the introduction needle septum 33B. At this time, the user peels a protective sheet of the adhesive pad 35 of the injection set 30 and the liquid transporting apparatus 1 may adhere to the living body by attaching the adhesive pad 35 to the skin of the living body.

Next, the user performs pre-operation of the driving section 5 so that the liquid for a capacity of a region (a region except the introduction septum) in which the introduction needle 32A is present is transported (S005). Therefore, it is possible to fill a space in which the introduction needle 32A is present with the liquid.

After that, the user makes the liquid transporting apparatus 1 perform a quantitative transport processing (a normal processing) (S006). At this time, in the liquid transporting apparatus 1, the cam 11 is rotated by driving the piezoelectric motor 121 of the driving mechanism 12, seven fingers 22 are pressed in order by the protrusion sections of the cam 11 and the tube 21 is closed in order from the upstream side in the transportation direction, and then the liquid is transported by writhing of the tube 21 in the quantitative transport processing, the rotation amount of the cam 11 is controlled so that the liquid of a predetermined amount is transported in a predetermined time.

Adjustment of Transporting Amount of Liquid

A normal liquid transportation operation using the liquid transporting apparatus 1 is performed by the quantitative transport processing (the normal processing) described in S006 of FIG. 12, but it may be necessary to change the liquid transport amount during the liquid transportation operation. For example, if the liquid transporting apparatus 1 is used as an insulin injecting apparatus, it is possible to continuously inject a certain amount of the insulin in the normal processing (hereinafter, such an injecting method is also referred to as "basal"). Meanwhile, since a blood glucose level increases temporarily when the user takes a meal, it is necessary to increase the injection amount of the insulin based on the increase in the blood glucose level (hereinafter, such an injecting method is also referred to as "bolus"). Then, the liquid transporting apparatus 1 performs processing (a transporting amount adjustment processing) that changes the liquid transport amount depending on situations.

The adjustment of the transporting amount is performed by controlling the operation of the driving section 5, based on a predetermined control pattern of the plurality of control patterns stored in the control substrate 15. For example, if the normal insulin injection of the user is 1 U (1 unit=approximately 10 μliters) per hour, an injection speed of 1 U/h is set as the control pattern for the basal. Further, if it is necessary to inject the insulin of 20 U (20 units) in a short term when taking a meal, the injection amount of 20 U is set as the control pattern for the bolus. Then, the insulin injection is normally performed at the injection speed of 1 U/h, based on the control pattern for the basal. Meanwhile, the control pattern for the bolus is operated and the insulin of 20 U is injected within 24 hours of taking a meal.

The settings described above are performed by the controller 50. In the example described above, the control pattern depending on the injection speed (1 U/h) of the insulin which is set for the basal and the control pattern depending on the injection amount (20 U) of the insulin which is set for the bolus are set by the controller 50. Further, for example, in a case where the user wants to change the control pattern, for example, it is possible to change the control pattern using the controller 50, even if the time when a meal is taken is changed or an intake amount of carbohydrate is great.

It is more convenient for the user to be able to appropriately adjust injection unit (the transporting amount of the liquid) of the insulin.

Adjustment of Transporting Amount of Liquid Using Function Button 145

In the example described above, the control pattern is changed and the transporting amount (the injection amount of the insulin) of the liquid is adjusted by the remote operation using the controller 50. However, the invention is not limited to the case where the user always holds the controller 50. For example, if the user goes out without carrying the controller 50, it is difficult to easily adjust the injection amount of the insulin, even if there is a need to change the control pattern somewhere.

Then, in the embodiment, it is possible to easily adjust the liquid transport amount in the liquid transporting apparatus by the single unit without using the external control device (the controller 50). Particularly, the liquid transport amount is changed by setting the function for changing the control pattern in the function button 145 included in the body 10 and by operating the function button 145.

Moreover, in the embodiment, the setting of the function of the function button 145 is performed by operating the operation button 51 by the user while recognizing the information displayed on the display section 52 of the controller 50. Therefore, even if the body 10 of the liquid transporting apparatus 1 does not include the display section, it is possible to accurately perform the setting of the function. Further, various types of functions are easily set in addition to the setting of the control patterns.

Figure 14:
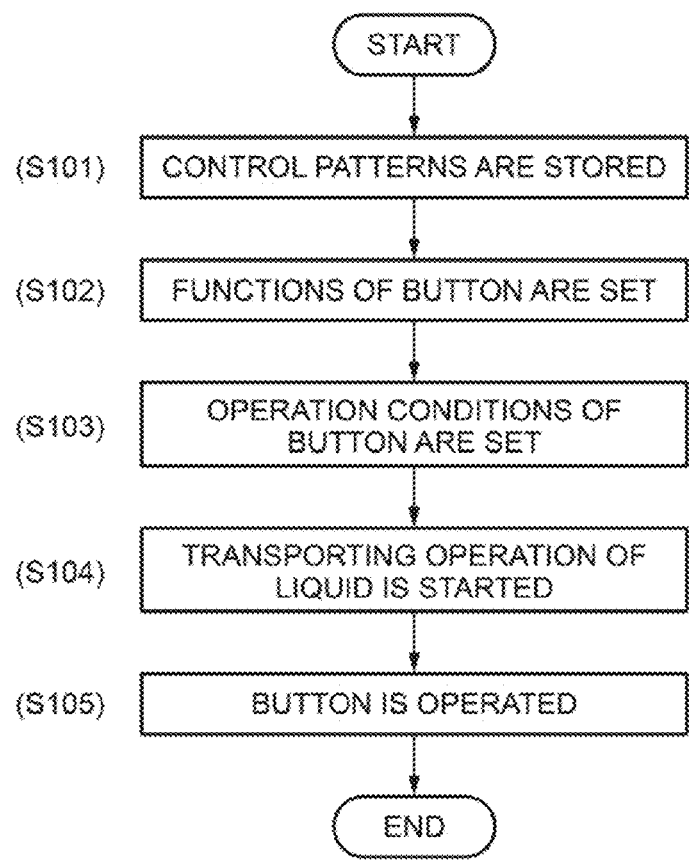
FIG. 14 is a flowchart when adjustment of a liquid transport amount is done using a function button.

FIG. 14 is a flowchart for performing the adjustment of the liquid transport amount by using the function button 145.

The user stores in advance a plurality of control patterns for controlling the driving section 5 in the control substrate 15 by using the controller 50 (S101). Especially, when using as the insulin injecting apparatus, at least two types of control patterns for the basal and the bolus may be stored.

Next, the user performs setting of the functions of the function button 145 by using the controller 50 (S102). In the embodiment, as the function of the function button 145, the function for changing the control pattern is set. For example, if the function button 145 is pressed when the operation of the liquid transporting apparatus 1 is controlled, based on the control pattern for the basal, the control pattern for the bolus from the plurality of types of the control patterns which are set in advance in S101 is selected. That is, it is possible to change the control pattern by pressing the function button 145 during the transporting operation of the liquid.

Moreover, in the function button 145, it is possible to set a plurality of functions in addition to the function which changes and performs the control pattern. For example, as the function of the function button 145, an emergency stop function to stop immediately the transporting operation of the liquid or a function to start the priming processing may be set. Since a plurality of functions can be set in the function button 145, it is possible to realize various types of functions in the liquid transporting apparatus 1 by the single unit, even if the user does not hold the controller 50. Further, a plurality of function buttons 145 are provided and different function may be set in each button.

Subsequently, the user performs the setting of operation conditions of the function button 145 (S103). The setting of the operation conditions sets conditions for realizing the functions which are set in the function button 145 in S102. If the user accidentally comes into contact with the function button 145 while performing the transporting operation of the liquid, there is a problem in that the control pattern is immediately changed and then the liquid transport amount is changed. For example, if the control pattern for the basal is changed to the control pattern for the bolus at unnecessary due to malfunction, it is impossible to appropriately perform the insulin injection due to a rapid increase in the injection amount of the insulin. Thus, occurrence of the malfunction is suppressed by setting the operation conditions of the function button 145 in the control section and by realizing a predetermined function depending on the operation condition which is set. In the embodiment, the function which is set is realized depending on a length of a time in which the function button 145 is pressed. Particularly, the operation condition is set so that the control pattern is changed by continuously pressing (long pressing) the function button 145 for a long time (for example, three seconds). However, the operation conditions are set in advance in a production stage of the liquid transporting apparatus and the user may not need to perform the setting of the operation conditions.

After that, the transporting operation of the liquid is started (S104) and the quantitative transport processing (the normal processing) is performed. Then, a predetermined function of the functions which are set in advance is activated by operating the function button 145 by the user at a necessary timing (S105). In the embodiment, a processing (an adjustment processing of the transporting amount) for changing from the liquid transporting amount in the basal to the liquid transporting amount in the bolus by pressing the function button 145 is performed.

In the liquid transporting apparatus (the insulin injecting apparatus) of the embodiment, the normal insulin injection is performed based on the control pattern for the basal, but the pattern is changed to the control pattern for the bolus by pressing the function button 145 by the user for a long time at the timing of taking a meal or the like. Therefore, even if the user does not carry the controller 50, it is possible to easily adjust the transporting amount (the injection amount of the insulin) of the liquid by the liquid transporting apparatus 1 by the single unit.

Further, since the display section such as display is not provided in the liquid transporting apparatus 1 and the liquid transport amount can be adjusted only by the operation of the button, it is possible to downsize and make the entire apparatus compact.

Second Embodiment

In a second embodiment, a function of catheter detaching detection is set in the function button 145.

Here, "the catheter detaching detection" is to detect whether or not the soft needle 31 (the catheter) detaches from the living body. If the soft needle 31 detaches from the living body, the liquid does not inject into the living body, even if the liquid transporting apparatus 1 transports the liquid. In the embodiment, in order to reduce the load on the living body, since the soft needle 31 having flexibility is being punctured, specifically, it is a state of easily detaching. Further, if the soft needle 31 is short to reduce the load on the living body, the soft needle 31 is in the state of easily detaching. Then, in the embodiment, whether or not the soft needle 31 detaches from the living body is monitored and the transportation of the liquid is performed after it is detected that the catheter does not detach from the living body.

Basic Configuration of Liquid Transporting Apparatus

In the second embodiment, the liquid transporting apparatus 1 has a determination section 70 that monitors the detaching of the soft needle 31. A basic configuration except the determination section 70 is subsequently similar to that of the first embodiment.

Figure 15:
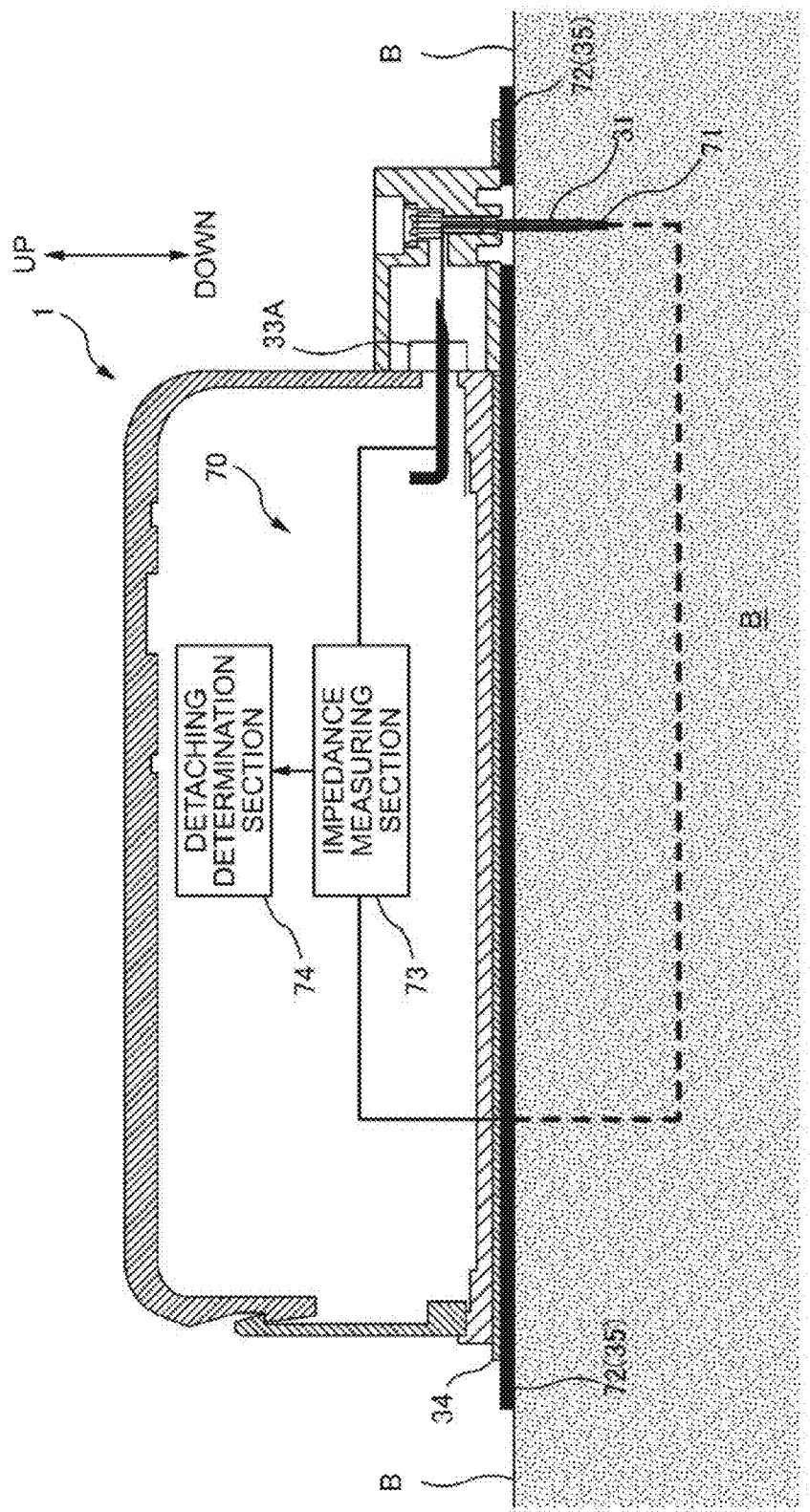
FIG. 15 is an explanatory view of a determination section.

FIG. 15 is an explanatory view of the determination section 70. Here, the liquid transporting apparatus 1 is adhered to a living body B. When the introduction needle 32A (see FIG. 3) is removed, the soft needle 31 punctures the living body. In the view, a conductive path is indicated in a dotted line through the living body B.

The determination section 70 has a first electrode 71, a second electrode 72, an impedance measuring section 73 and a detaching determination section 74. The impedance measuring section 73 and the detaching determination section 74 are provided in the control substrate 15 described above.

The first electrode 71 is a tubular electrode provided in the leading end section of the soft needle 31 and configures a part of the flow path in which the liquid is transported by coming into contact with the liquid in an inner periphery section thereof. Since the first electrode 71 directly comes into contact with the liquid, error can be reduced when measuring the impedance and measurement accuracy is improved compared to a case where the electrode performs capacitive coupling with the liquid (a case where the electrode is provided outside the tube and the electrode does not come into direct contact with the liquid).

The second electrode 72 is an electrode which is disposed by coming into contact with the skin of the living body B. Specifically, the second electrode 72 also serves as the adhesive pad 35 and the adhesive pad 35 is configured of a conductive pad having an adhesive surface.

Moreover, in order to electrically connect the impedance measuring section 73 which is provided in the control substrate 15 on the side of the body 10 to the first electrode 71 (the leading end section of the soft needle 31), a connection terminal (not illustrated) is formed between the body 10 and the soft needle 31. Further, in order to electrically connect the impedance measuring section 73 which is provided in the control substrate 15 on the side of the body 10 to the second electrode 72 (the adhesive pad 35), connection terminals (not illustrated) are formed between the body 10 and the cartridge 20, and between the cartridge 20 and the injection set base 34.

The impedance measuring section 73 measures the impedance between the first electrode 71 and the second electrode 72. As illustrated in the view, if the soft needle 31 punctures the living body B, since a closed circuit is configured through the living body B, if AC voltage (for example, frequency of approximately 1 kHz to 10 kHz) is applied to the first electrode 71 and the second electrode 72, the impedance measuring section 73 measures the impedance of a predetermined expected range (for example, approximately tens of kΩ to hundreds of kΩ). Meanwhile, if the soft needle 31 detaches from the living body B, since the closed circuit is not configured and a current is not flowed, the impedance measuring section 73 measures high impedance (for example, 10 MΩ or more).

The detaching determination section 74 determines the detaching of the soft needle 31, based on a result of measurement in the impedance measuring section 73. Specifically, if the impedance of the result of the measurement is lower than a predetermined threshold, the detaching determination section 74 determines that the soft needle 31 normally punctures the living body B. Further, if the impedance of the result of the measurement is higher than a predetermined threshold, the detaching determination section 74 determines that the soft needle 31 detaches from the living body B. Then, the detaching determination section 74 outputs the result of the measurement to the control section of the control substrate 15.

Operation when Performing Catheter Detaching Detection

Figure 16:
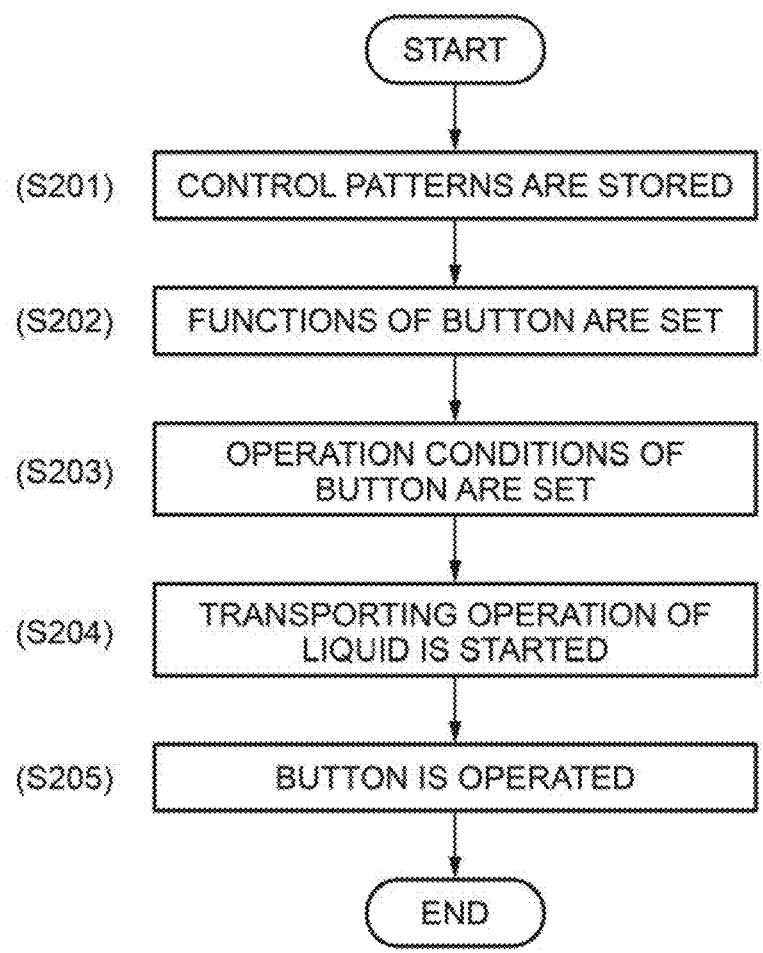
FIG. 16 is a flowchart when performing detection of detaching of a catheter in a second embodiment.

FIG. 16 is a flowchart for performing the catheter detaching detection in the second embodiment. Similar to the first embodiment, first, the user stores a plurality of types of control patterns for controlling the driving section 5 in the control substrate 15 by using the controller 50 (S201).

Figure 17:
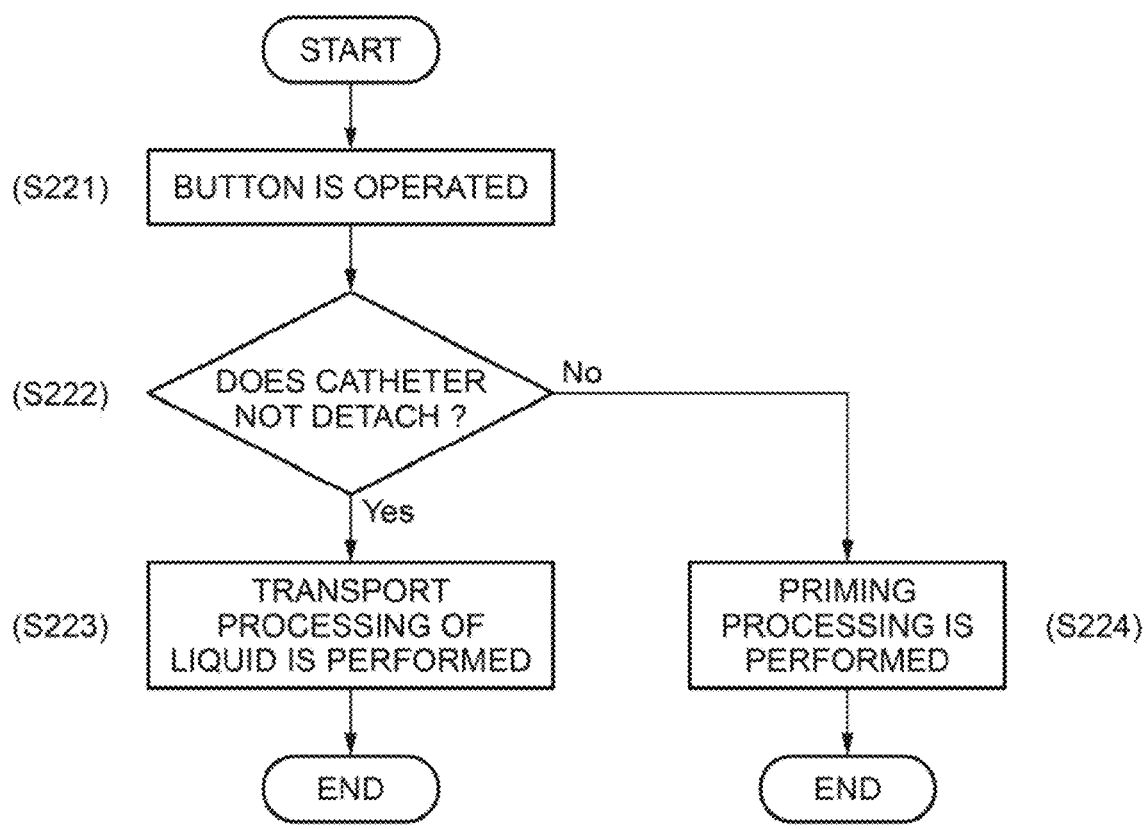
FIG. 17 is a view describing functions which are set in a function button in the second embodiment.

Next, setting of the functions of the function button 145 is performed (S202). In the embodiment, the catheter detaching detection is performed by pressing the function button 145 and different function is realized, based on the result thereof. FIG. 17 is a view describing the functions which are set in the function button 145 in the second embodiment. In the embodiment, if the user performs the button operation (that is, the function button 145 is pressed) (S221), as described above, the catheter detaching determination is performed by the determination section 70 (S222).

As a result of the determination, if it is determined that the catheter (the soft needle 31) does not detach (Yes in S222), that is, if it is determined that the catheter is normally mounted on the body of the user, the normal transport processing of the liquid is performed (S223). If the catheter is normally mounted on the body of the user, since the injection operation of the liquid can be safely performed, the normal injection operation of the liquid is performed as is.

Meanwhile, as a result of the determination, if it is determined that the catheter (the soft needle 31) detaches (No in 3222), the priming processing is performed (S224). If the catheter detaches from the body, possibility that gas is entrained in the flow path of the liquid inside the catheter is high. Thus, the function button 145 is used for performing the priming processing and discharges gas inside the flow path. Then, the catheter punctures against the living body by using the introduction needle 32A again after the priming processing is performed. Moreover, if it is determined that the catheter is normally mounted on the body of the user after the priming operation is performed, the setting may be performed so as to automatically stop the priming operation.

The determination of the detaching of the catheter is performed and the function button 145 is set so as to perform appropriate processing, based on the result thereof. Therefore, it is possible to further effectively use the liquid transporting apparatus depending on different situations.

Next, setting of operation conditions of the function button 145 is performed (S203). In the second embodiment, the determination of the detaching the catheter is performed by the determination section 70 by continuously pressing the function button 145 for a long time (for example, 3 seconds), and the conditions are set so as to perform the transport processing of the liquid or the priming processing, based on the result of the determination, as described in FIG. 17. Therefore, the malfunction or the like such as erroneously pressing the button is suppressed. Further, in the example described above, if it is determined that the catheter detaches, the priming processing is performed, but at this time, the setting may be performed so that the priming processing is continued while the function button 145 is pressed. In this way, gas entrained inside the flow path of the liquid is further easily discharged.

After the setting is complete, the liquid transportation operation is started (S204) and the function which is set in advance is activated by operating the function button 145 by the user at a necessary timing (S205). In the example described above, the determination of the detaching of the catheter is performed by pressing the function button 145 and the normal transport processing of the liquid or the priming processing is performed, based on the result of the determination.

Moreover, in the embodiment, an entire surface of the adhesive pad 35 has conductivity, but only a part of the adhesive pad 35 has the conductivity and the portion having the conductivity may also be the second electrode 72. In this case, it is preferable that the second electrode 72 be a center section of the adhesive pad 35 by having the conductivity only in the center section of the adhesive pad 35 (by not having the conductivity in a peripheral section of the adhesive pad 35). Therefore, even if a part of the peripheral section which does not have the conductivity is peeled, there is an effect which is unlikely to affect the measurement of the impedance.

Further, in the embodiment, the AC voltage is applied in a state where a DC component of the voltage of the power source of the impedance measuring section 73 is cut so that a bias voltage is not applied between the first electrode 71 and the second electrode 72. For example, if the DC voltage is applied between the first electrode 71 and the second electrode 72, an electrochemical process may occur in the liquid (the liquid between the first electrode 71 and the second electrode 72) coming into contact with the electrode, characteristics of the liquid may be changed or deposits may attach to the electrode.

Modification Example

Figure 18:
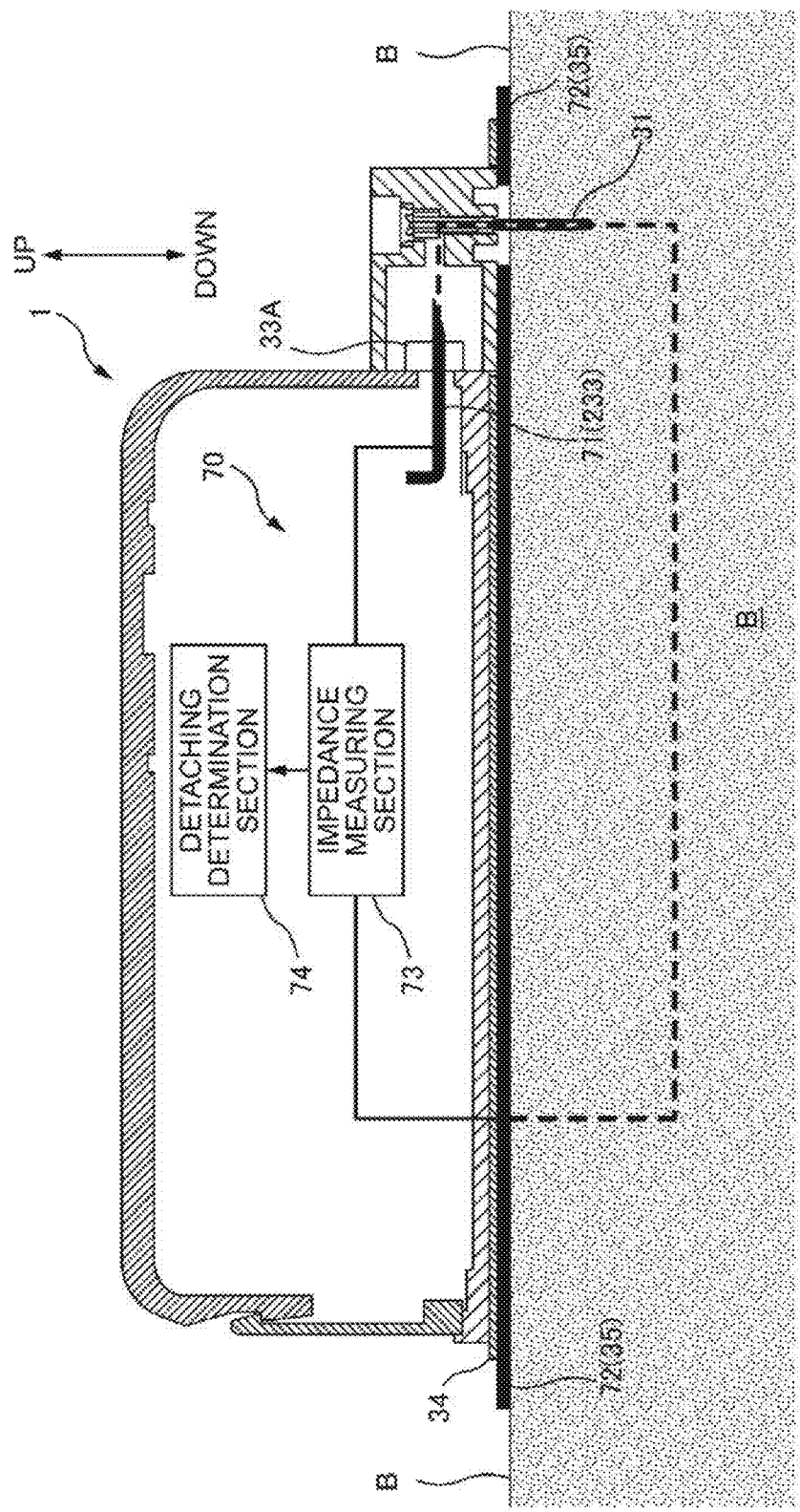
FIG. 18 is a view describing a determination section of a modification example.

In the second embodiment, the position of the electrode of the determination section 70 may be changed. FIG. 18 is a view describing a determination section 70 of a modification example.

In the modification example, the first electrode 71 is provided in the connection needle 233. Particularly, the first electrode 71 also serves as the connection needle 233 and the connection needle 233 is configured of a conductive metal. Since an inner periphery surface of the connection needle 233 configures the flow path by coming into direct contact with the liquid, it is possible to use the connection needle 233 as the electrode. At this time, a point that it is necessary to provide the first electrode 71 on the downstream side of the region in which the fingers 22 press the tube 21 should be noted. For example, if the first electrode 71 is provided on the upstream side of the fingers 22, when the fingers 22 close the tube 21, the liquid may be insulated in the closed position and, as a result, the impedance may increase between the first electrode 71 and the second electrode, and then the determination of the detaching cannot be performed, based on the impedance. Moreover, also in case of FIG. 15 described above, since the first electrode 71 is provided in the leading end section of the soft needle 31, the fingers 22 are disposed on the downstream side of the region in which fingers 22 press the tube 21.

Each configuration except the first electrode 71 is similar to that of FIG. 15. Then, if the soft needle 31 punctures the living body B, the closed circuit is configured through the liquid and the living body B. The impedance measuring section 73 determines the detaching of the catheter (the soft needle) by measuring the impedance of a predetermined range by applying the AC voltage to the first electrode 71 (the connection needle 233) and the second electrode 72 (the adhesive pad 35).

According to the modification example, since the electrode can be common with the connection needle 233, a structure of the entire apparatus is simplified and the costs can be reduced.

Other Embodiments

The embodiments described above are intended to facilitate understanding of the invention and are not intended to be constructed as limiting the invention. The invention may be altered and improved as long as there is no departure from the spirit thereof, and it is needless to say that equivalents thereof are included in the invention.
Electrode In the second embodiment described above, the first electrode serves as the leading end section of the soft needle 31 or the connection needle 233 and the second electrode serves as the adhesive pad 35, but the first electrode or the second electrode is not limited to the embodiment.

For example, the first electrode may be the discharge-side joint 232. However, in this case, since the first electrode is disposed separate from the living body than the embodiments described above, error is likely to occur in the measurement of the impedance.

Further, the first electrode and the second electrode do not serve as other configuration elements and may be provided independently. However, in this case, the number of parts increases to more than that of the embodiments described above.

The entire disclosure of Japanese Patent Application No. 2013-051378, filed Mar. 14, 2013 is expressly incorporated by reference herein.

What is claimed is:
1. A liquid transporting apparatus comprising:
a driving mechanism;
a tubular portion configured to hold a liquid and transport a liquid when squeezed or writhed by the driving mechanism;
a needle configured to supply the liquid from the tubular portion to a living body;
a memory configured to store a plurality of control patterns that control squeezing or writhing the tubular portion;
a control device that is configured to: control the driving mechanism to squeeze or writhe the tube based on a control pattern;
a detachment determining section that is configured to determine whether the needle is detached from the living body;
a body case configured to house the driving mechanism, the tubular portion, the memory and the control device; and
a button provided on an outer surface of the body case, wherein the control device is configured to, upon detection of the button being touched continuously for a predetermined amount of time:
determine, from the detachment determination section, whether the needle is detached from the living body; and
if the needle is not detached from the living body, switch the control pattern to another control pattern of the plurality of control patterns for controlling the driving mechanism.

2. The liquid transporting apparatus according to claim 1, wherein the control device is further configured to: change the control pattern by setting a plurality of functions, wherein one function of the plurality of functions is set based on a received user input.

3. The liquid transporting apparatus according to claim 2, wherein the control device is further configured to set one function of the plurality of functions based on a length of time of the touch of the button.

4. The liquid transporting apparatus according to claim 2, wherein the one function of the plurality of functions is set by an external remote control device.

5. The liquid transporting apparatus according to claim 2, wherein the one function of the plurality of functions adjusts a liquid transport amount by changing the control pattern or stopping the transportation of the liquid.

6. A liquid transporting method comprising:
transporting a liquid by squeezing or writhing a tubular portion configured to hold the liquid;
controlling, via a control device, a driving mechanism to squeeze or writhe the tubular portion based on a control pattern; and
upon detection of a button, which is attached to a body case that is configured to house the driving mechanism, the tubular portion, a memory and the control device, being touched continuously for a predetermined amount of time:
determining whether a needle that is configured to supply the liquid from the tubular portion to a living body is detached from the living body; and
if the needle is not detached from the living body, switching, via the control device, the control pattern to another control pattern of a plurality of control patterns for controlling the driving mechanism that are stored in a memory.

7. The liquid transporting apparatus according to claim 1, wherein the liquid is transported by squeezing the tubular portion by driving a plurality of fingers.

8. The liquid transporting apparatus according to claim 1, further comprising a cam, wherein a center of a circle of the tubular portion is coincident with a rotation center of the cam.

9. The liquid transporting apparatus according to claim 7, wherein the tubular portion has elasticity enough to be closed when being pressed by a finger and to be returned to an original position when releasing a force from the finger.

10. The liquid transporting apparatus according to claim 7, wherein the fingers are operated in a driven basis by receiving a force from a centralized cam.

11. The liquid transporting apparatus according to claim 10, wherein
each of the plurality of fingers has a rod-shaped shaft section and a collar-shaped pressing section, and is a T-shape,
each of the rod-shaped shaft sections comes into contact with the centralized cam, and
each of the collar-shaped pressing sections comes into contact with the tubular portion.

12. The liquid transporting apparatus according to claim 10, wherein the plurality of fingers are radially disposed between the centralized cam and the tubular portion at an equal distance from a rotation center of the centralized cam.

13. The liquid transporting apparatus according to claim 1, wherein the driving mechanism further comprises a plurality of reciprocating fingers attached to a centralized hub.

14. The liquid transporting apparatus according to claim 13, wherein the reciprocating fingers operate in a sequential manner to provide the drive for the squeezing or writhing.

15. The liquid transporting apparatus according to claim 1, further comprising a cartridge, wherein the tubular portion is partially disposed in a circular arc shape along an inner surface of a tube guide wall of the cartridge.

16. The liquid transporting apparatus according to claim 15, wherein
the portion of the circular arc shape of the tubular portion is disposed between the inner surface of the tube guide wall and a plurality of fingers, and
a center of a circle of the tubular portion is coincident with a rotation center of the cam.

17. A liquid transporting apparatus comprising:
a body comprising:
a driving mechanism;
a tubular portion configured to hold a liquid and transport a liquid when squeezed or writhed by the driving mechanism;
a needle configured to supply the liquid from the tubular portion to a living body;
a memory configured to store a plurality of control patterns that control squeezing or writhing the tubular portion;
a button attached to the body; and
a control device that is configured to:
control the driving mechanism to squeeze or writhe the tube based on a control pattern; and
when a signal indicating that the button has been touched continuously for a predetermined amount of time is received:
determine whether the needle is detached from the living body; and
if the needle is not detached from the living body, switch the control pattern to another control pattern of the plurality of control patterns for controlling the driving mechanism.

18. The liquid transporting apparatus according to claim 1, further comprising two electrodes, wherein
the detachment determination section includes an impedance measuring section, which is used to make the determination of whether the needle is detached from the living body, and
the impedance measuring section is configured to measure the impedance between the two electrodes.

19. The liquid transporting apparatus according to claim 18, wherein the impedance measuring section:
determines whether an impedance of a result of the measurement is lower than a predetermined threshold, and
if the impedance is lower than the predetermined threshold, determines that the needle is not detached from the living body.

20. The liquid transporting apparatus according to claim 18, wherein
a first electrode of the two electrodes serves as a leading section of the needle, and
a second electrode of the two electrodes serves as an adhesive pad.

* * * * *